(12) United States Patent
Carrano et al.

(10) Patent No.: US 10,717,080 B2
(45) Date of Patent: Jul. 21, 2020

(54) SYSTEMS AND METHOD FOR METERING AND TIMING OF FLUID FLOW IN A POINT-OF-CARE DIAGNOSTIC CARTRIDGE

(71) Applicant: Paratus Diagnostics, LLC, San Marcos, TX (US)

(72) Inventors: John Jacob Carrano, San Marcos, TX (US); John Carrano, San Marcos, TX (US); Nicole Plata, San Marcos, TX (US)

(73) Assignee: PARATUS DIAGNOSTICS, LLC, San Marcos, TX (US)

( * ) Notice: Subject to any disclaimer, the term of this patent is extended or adjusted under 35 U.S.C. 154(b) by 0 days.

(21) Appl. No.: 16/122,835

(22) Filed: Sep. 5, 2018

(65) Prior Publication Data
US 2020/0070156 A1 Mar. 5, 2020

(51) Int. Cl.
| | |
|---|---|
| *B01L 3/00* | (2006.01) |
| *G01N 33/577* | (2006.01) |
| *B01L 9/00* | (2006.01) |
| *G01N 33/535* | (2006.01) |
| *G01N 21/76* | (2006.01) |
| *G01N 35/00* | (2006.01) |

(52) U.S. Cl.
CPC ... *B01L 3/502715* (2013.01); *B01L 3/502746* (2013.01); *B01L 9/527* (2013.01); *G01N 33/535* (2013.01); *G01N 33/577* (2013.01); *B01L 2300/0627* (2013.01); *B01L 2400/0677* (2013.01); *G01N 21/76* (2013.01); *G01N 35/00871* (2013.01)

(58) Field of Classification Search
None
See application file for complete search history.

(56) References Cited

U.S. PATENT DOCUMENTS

| | | | |
|---|---|---|---|
| 2006/0090800 A1* | 5/2006 | Banerjee | B01L 3/502738 137/827 |
| 2016/0279634 A1* | 9/2016 | Stemme | B01L 3/502738 |

* cited by examiner

*Primary Examiner* — Paul S Hyun
(74) *Attorney, Agent, or Firm* — Cronin PLLC; Aaron Pickell

(57) ABSTRACT

A specimen processing cartridge includes a reservoir having a fluid inlet, an elastic diaphragm, and a fluid outlet. The reservoir is operable to receive a volume of liquid from the fluid inlet, and the fluid outlet is positioned along a fluid flow path between the reservoir and a downstream reservoir. The cartridge includes a dissolvable membrane that occludes flow through the fluid outlet when the dissolvable membrane is in a first, undissolved state, and that permits flow from the reservoir to the downstream reservoir when in a second, dissolved state. The elastic diaphragm is operable to pressurize the reservoir upon receiving the volume of liquid when the dissolvable membrane is in the first, undissolved state, and is operable to contract and propel at least a portion of the volume of liquid from the reservoir to the downstream reservoir when the dissolvable membrane is in the second, dissolved state.

16 Claims, 8 Drawing Sheets

SYSTEMS AND METHOD FOR METERING AND TIMING OF FLUID FLOW IN A POINT-OF-CARE DIAGNOSTIC CARTRIDGE

TECHNICAL FIELD

The present disclosure relates generally to the field of medical diagnostics and more particularly to in vitro medical diagnostic devices including point-of-care in vitro medical diagnostic devices.

BACKGROUND OF THE INVENTION

There is a recognized and compelling need for the rapid and accurate diagnosis of common infectious diseases in an out-patient setting. This need results from a rapidly emerging trend toward what is sometimes referred to as "patient centric care" in which convenience along with better health outcomes and low cost—becomes a key market driver.

The field of in vitro diagnostics is well established, with many manufacturers and a wide spectrum of products and technologies. The testing for infectious pathogens in human patient specimens is largely confined to centralized laboratory testing in Clinical Laboratory Improvement Amendment (CLIA) rated medium-complexity or high-complexity facilities. Commonplace techniques used in such laboratories include traditional culturing of specimens, immunological assaying using Enzyme-Linked Immunosorbent Assay (ELISA), nucleic acid testing (such as polymerase chain reaction, PCR), and other methods.

Many different types of devices can be used to complete diagnostic processes in centralized laboratories. It has been historically difficult, however, to complete such diagnostic processes entirely, or almost-entirely in an outpatient setting where equipment and materials that are common-place in a laboratory may not be readily available or are suitable for use. As a result, relatively few devices are readily available that are able to complete diagnostic processes in the field (meaning outside of a laboratory environment) without access to the resources of a laboratory.

SUMMARY

Figure 1:
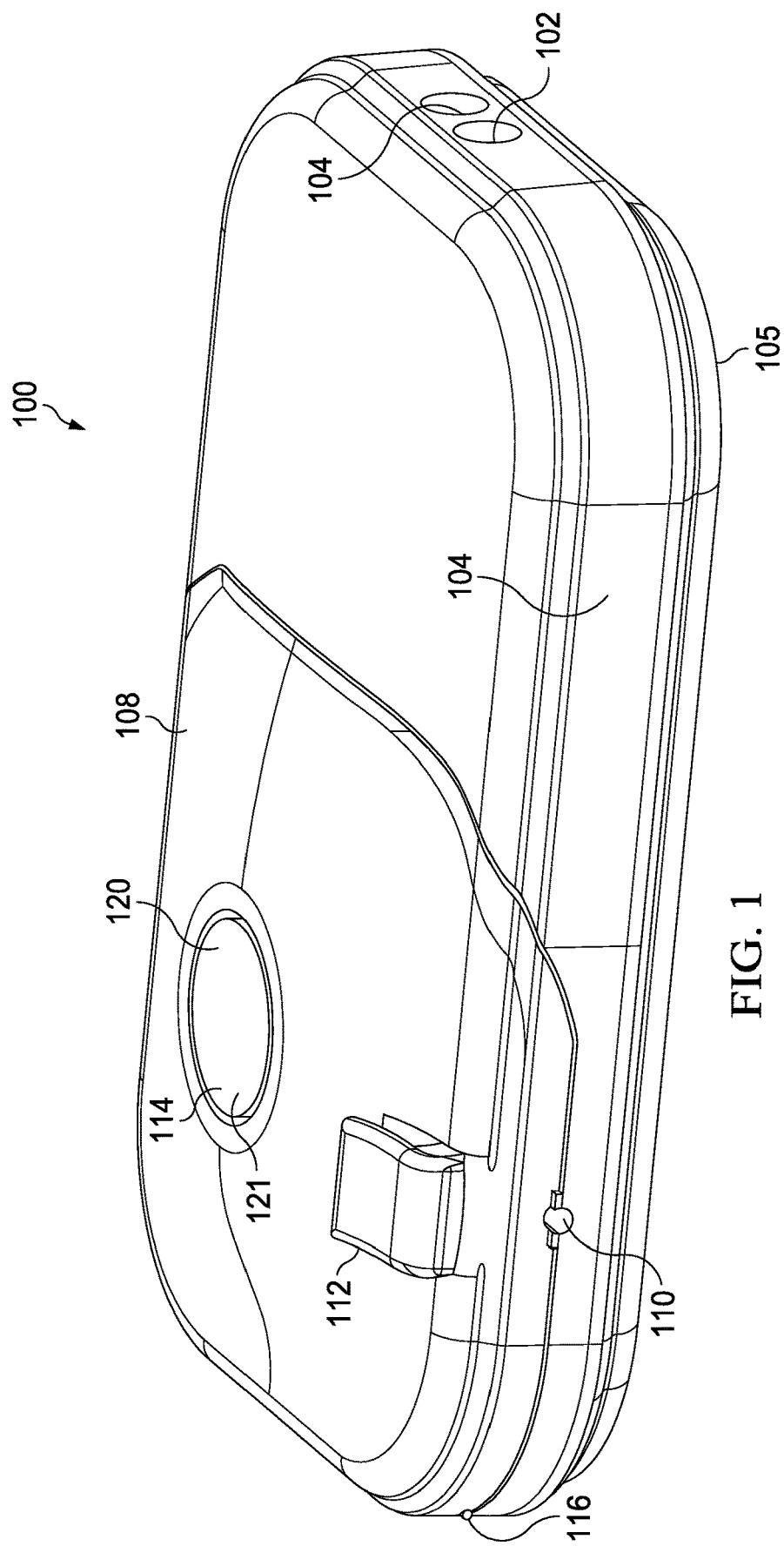
FIG. 1 is a schematic, perspective view of an illustrative embodiment of a specimen delivery cartridge.

In accordance with an illustrative embodiment, a specimen processing cartridge includes a reservoir having a fluid inlet, an elastic diaphragm, and a fluid outlet. The reservoir is operable to receive a volume of liquid from the fluid inlet, and the fluid outlet is positioned along a fluid flow path between the reservoir and a downstream reservoir. The cartridge includes a dissolvable membrane that occludes the fluid outlet when the dissolvable membrane is in a first, undissolved state, and that permits flow from the reservoir to the downstream reservoir when in a second, dissolved state. The elastic diaphragm is operable to pressurize the reservoir upon receiving the volume of liquid when the dissolvable membrane is in the first, undissolved state. The elastic diaphragm is operable to contract and propel at least a portion of the volume of liquid from the reservoir to the downstream reservoir when the dissolvable membrane is in the second, dissolved state.

In accordance with another illustrative embodiment, a method for implementing a diagnostic process includes delivering a volume of liquid to a reservoir of a diagnostic device via a fluid inlet. The diagnostic device includes the reservoir, an elastic diaphragm positioned within a boundary of the reservoir, a fluid outlet port positioned along a fluid flow path from the reservoir to a downstream reservoir, and a dissolvable membrane that occludes the fluid flow path when the dissolvable membrane is in a first, undissolved state, and that permits flow from the reservoir to the downstream reservoir when in a second, dissolved state. The method further includes applying a positive pressure to the reservoir, thereby causing expansion of the elastic diaphragm when the dissolvable membrane is in the first, undissolved state, and exposing the dissolvable membrane to the volume of liquid. The dissolvable membrane dissolves after a predetermined amount of time lapses following exposure to the volume of liquid, and dissolution of the dissolvable membrane permits the elastic diaphragm to contract and propel at least a portion of the volume of liquid from the reservoir to the downstream reservoir.

DETAILED DESCRIPTION

Conventional models for infectious disease diagnosis rely heavily on centralized laboratory testing (e.g. culture), which can often take two to four days to provide a reliable result. A consequence of conventional models is that patients are not necessarily properly diagnosed on their first visit; nor are they given the correct drug prescription. This can result in money wasted on either incorrect or unnecessary prescriptions, inconvenience to patients owing to repeat visits, and even the potential for otherwise treatable illnesses to progress to more serious conditions requiring expensive hospital stays. In diagnosing a patient, it is common for a physician to ask whether an illness is the consequence of a bacterial or a viral pathogen. In seeking to answer the foregoing question, incomplete or inaccurate diagnoses can result in the over-prescription of antibiotics, which is a cost burden to the healthcare system. Perhaps more importantly, incorrect diagnoses may contribute to the increasing frequency of antibiotic resistant strains in the community, which is a national health concern.

Seeking to improve upon the conventional model, some rapid diagnostic tests (RDTs) have been brought to market for use in an out-patient setting. Many of these RDTs, however, are simple "rule-in/rule-out" tests which do not necessarily inform clinical decision-making. Many such RDTs also suffer from poor sensitivity and specificity, making the validity and clinical utility of their results unreliable. The present disclosure relates to a system that is able to provide accurate diagnoses during a patient visit and with a high degree of accuracy.

The present disclosure provides for a point-of-care diagnostic device for use in determining the presence of a target infectious disease in a biological specimen. The illustrative embodiments provide a low complexity and low-cost solution while providing a mechanism for improving health outcomes as compared to the state of the art. Further, to leverage the ubiquity of smartphones and other computing devices in common use globally, an illustrative specimen processing cartridge may facilitate the use of a computing device, such as a smartphone, to carry out certain processes in testing for one or more pathogens.

More particularly, the present disclosure relates to a specimen processing cartridge that may be deployed in any useful context, but is described in the present disclosure in the context of processing a biological specimen. In some illustrative embodiments, the cartridge provides a flow channel that may be populated with reagents or coupled to one or more fluid inlets to receive reagents from different reservoirs and facilitate wicking or capillary flow across a viewing area. In an exemplary embodiment, different reagents may be introduced to a viewing area using different methods. Various liquids, which may include the reagents, flow across a main channel of flow through the viewing area at different times to facilitate execution of a diagnostic test.

The differing reagents may be introduced at different times to allow for sufficient time for the occurrence of reaction with embedded reagents on a substrate or capillary plate apparatus positioned within the main channel. As referenced herein, a capillary plate apparatus is intended to describe a structure comprising offset surfaces that are separated by a relatively short distance to form a channel between the surfaces that facilitates capillary flow. The offset surfaces may be substantially parallel or may be out of parallel and merely sufficiently close to one another to facilitate capillary flow across the channel. Correspondingly, the referenced plates should also be understood to be members having opposing surfaces that may or may not be planar, as may be variable configurations (e.g., contoured surfaces or surfaces having a variable offset) in which the plates facilitate capillary flow but are not necessarily planar or parallel to each other. The channel may be open at the sides or enclosed. For example, side seals or a contiguous portion of material may be present at the sides of the channel to provide an enclosure.

In embodiments including a capillary plate apparatus, the apparatus may be formed from opposing (possibly parallel) plates that form a capillary channel and are optimized to facilitate viewing of one or more identified viewing areas, or detection zones of the capillary plate apparatus. As referenced herein, a detection zone is a portion of the flow channel that is viewable by a user or computing device of a user to perform at least a portion of an assaying process. The detection zone may include one or more detection locus (or loci), as described in more detail below.

The present disclosure also relates to a specimen processing cartridge having functionality that provides for the timing and metering of the delivery of liquids to a testing area. An exemplary cartridge may include a plurality of reservoirs for storing and processing liquids as they flow toward the testing area. For example, the cartridge may include a downstream reservoir that holds a sample collection liquid after the sample collection liquid has been interacted with a sample until the cartridge is placed in a specific wicking orientation. Placement of the cartridge in the wicking orientation may result in liquid in the downstream reservoir contacting a wicking substrate that carries the liquid along a fluid flow path across the testing area.

The specimen processing cartridge may also store one or more liquids that may be mixed together in an intermediate reservoir. Placement of such a processing cartridge in the wicking orientation may result in a secondary liquid in the intermediate reservoir contacting a dissolvable membrane that is configured to dissolve after a predetermined amount of time based on the composition and thickness of the membrane. The predetermined amount of time may correspond to the amount of time it takes for the sample collection liquid to evacuate the downstream reservoir. Expiration of the predetermined amount of time may allow additional time for the sample collection liquid to interact with reagents or other diagnostic materials at the testing area before additional flow is permitted from the intermediate reservoir to the downstream reservoir. This allows for the timed sequencing of flows across the viewing area.

The dissolvable membrane may rupture after the expiration of the predetermined amount of time, thereby permitting the secondary liquid to flow into the downstream reservoir, and ultimately to the testing area via the wicking substrate. Flow from the intermediate reservoir to the downstream reservoir may be aided by an expandable diaphragm, which expands when the secondary liquid is forced into the intermediate reservoir, which is already occupied by air or another suitable gas, and contracts to propel the secondary liquid from the intermediate reservoir when the dissolvable membrane ruptures. By expanding in the described manner, the expandable diaphragm allows for the displacement of air in the intermediate reservoir (into the increased volume provided by expansion of the diaphragm) when the secondary fluid is forced into the intermediate reservoir.

Referring now to the figures, FIG. 1 shows an illustrative embodiment of a specimen processing cartridge 100. The processing cartridge 100 may operate to further process a specimen that has already been subject to prior processing steps or to process a specimen that has recently been gathered from a patient. To that end, this disclosure is not intended to be limited in its application to a specimen processing cartridge 100 whose processing capability is limited to what is described. Rather, the disclosure is intended to illustrate the operative capabilities of the described specimen delivery cartridge, with an understanding that discrete portions of the illustrative specimen processing cartridge 100 may have independent utility if deployed in alternative apparatus. For example, a capillary plate apparatus may be deployed in an alternative device that uses mechanisms and features other than those described herein to supply liquids to the fluid inlet of any type of downstream apparatus.

In the specimen processing cartridge 100 of FIGS. 1-7. The specimen delivery cartridge 100 includes a cartridge body 106, which may be alternatively referred to as a first portion, and a lid 108, which may be alternatively referred to as a second portion. The lid 108 is coupled to the body 106 at a hinge 116. The lid 108 closes toward the body 106 to enclose a shaft port 110 for receiving a specimen collection device, such as a swab. The specimen collection device may be used to deliver a biological specimen or sample taken from a patient, such as saliva, a tissue sample, or a sample of bodily fluids.

Figure 2:
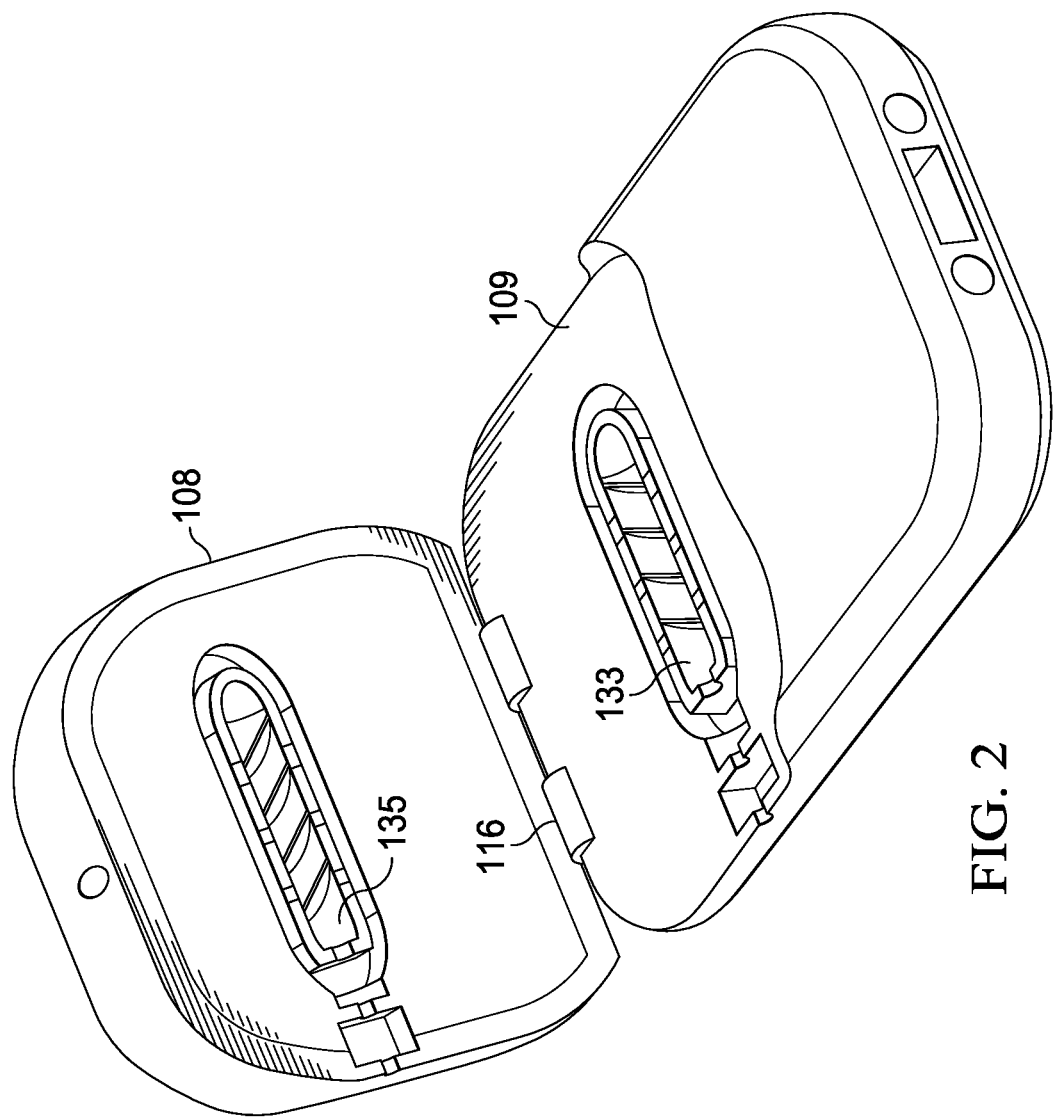
FIG. 2 is a schematic, perspective view of the specimen delivery cartridge of FIG. 1 in an open configuration.

FIG. 2 shows the specimen delivery cartridge 100 with the lid 108 open. The specimen delivery cartridge 100 may be understood as including a housing 105 that is made up of the body 106 and lid 108. The housing 105 has an open state and a closed state, and may be closed by moving the lid 108 toward the body 106 to transition from the open state to the closed state. The housing 105 includes an intermediate member 109 having a first cavity 133 that mates with a second cavity 135 formed in the lid 108 to form a specimen receiving chamber 134.

The specimen delivery cartridge 100 is shown as including a first actuation port 102 and second actuation port 104. The actuation ports may be operable to receive actuation posts or prongs from a mating adapter or similar device to actuate an internal fluid flow process, as described in more detail below. The specimen delivery cartridge 100 is also shown as including an actuator 114 which may form a portion of a first reservoir 120, which may be a "collection fluid reservoir" such that the actuator 114 may be depressed by a user to initiate a fluid flow process (as also described in more detail below). To that end, the actuator 114 is operable to move fluid a sample collection liquid within the specimen delivery cartridge 100 when the housing 105 is in the closed state and the actuator 114 is depressed or otherwise actuated. In the illustrated embodiment, the actuator 114 is a bulb-type actuator. In other embodiments, a piston-cylinder, electronic actuator, or other suitable type of actuator may be used.

The sample collection liquid may be stored within the first reservoir 120 prior to actuation and held in place by a destructible seal that prevents the sample collection liquid from exiting the first reservoir 120 through a port that is fluidly coupled to the specimen receiving chamber 134 while the seal is intact. Actuation of the actuator 114 may result in destruction (e.g., by pressurization or otherwise) of the destructible seal to allow for the communication of sample collection liquid from the first reservoir 120 to the specimen receiving chamber 134. A locking mechanism to hold the actuator 114 in the engaged position, or a check valve may be included at the referenced port so that once the actuator 114 has been engaged and sample collection liquid evacuated from the first reservoir 120, the sample collection liquid may not return to the first reservoir 120.

In some embodiments, the first reservoir 120 may be a blister pack. In others, the first reservoir 120 may be a cylinder, a liquid-filled bulb, or other similar container that may be evacuated when a hydraulic force is applied upon actuation by the actuator 114. The first reservoir 120 may be pre-filled with a sample collection liquid, which is a fluid that is selected to strip sample from a specimen collection device and carry the sample in suspended, diluted, or dissolved form through the fluid flow paths described below. The sample collection liquid may include a reagent such as a lysing agent to react with the sample, an elution buffer, an anti-coagulant or a solvent. The actuator 114 is operable to generate a hydraulic force to propel the sample preparation fluid from the first reservoir, through a tube, and through the specimen receiving chamber 134, and ultimately to a third reservoir 130, which may also be referred to as a "downstream reservoir."

The specimen receiving chamber 134 may be sized and configured to receive a specimen collection device (e.g., a swab) and facilitate extraction of the sample from the specimen collection device. In some embodiments, the specimen receiving chamber 134 includes features that roil the sample collection liquid passing through the specimen receiving chamber 134. As referenced herein, "roiling" refers to the manipulation of a fluid in a manner that induces turbulence or increased fluid shear forces to facilitate extraction of a specimen for analysis from a specimen collection device. For example, the specimen receiving chamber 134 may include helical or spiral features that induce vortex flow or spiral-like flow patterns, such as grooves. Such features may induce high fluid shear forces in the sample preparation fluid, increase turbulent energy and result in a higher Reynolds number. The foregoing characteristics may be understood to enhance the ability to extract a specimen for analysis from a specimen collection device placed in the chamber. In some embodiments, the roiling features may be spiralized grooves that engage or nearly engage the shaft of the specimen collection device to force the sample preparation fluid to follow a helical flow path through the sample collection portion of the specimen collection device as it is propelled through the specimen receiving chamber 134. For clarity, it is noted that in the context the sample preparation described in this disclosure, "extraction" does not relate to pulling DNA from a cell. Instead, "extraction" refers generally to the ability to recover organisms, molecules or other particles of interest off from a collection device and deliver those particles to a subsequent stage for further analysis.

The shaft portion of a swab or other suitable sample collection device may be deemed a nuisance once the sample is acquired and placed within the specimen processing cartridge 100. To facilitate removal of the portion of the shaft that extends beyond the housing 105 of the specimen processing cartridge 100, a swab may have a pre-scored shaft to facilitate breaking off the protruding portion of the swab shaft. Alternatively, the specimen processing cartridge 100 may include a swab cutter 112 to neatly trim away excess swab shaft material. Moreover, a swab shaft seal may be included where the shaft is inserted into the housing 105 of the specimen processing cartridge 100 and the adjoining external boundaries of specimen receiving chamber 134 may include a similar gasket or other suitable seal to form a sealed liquid flow path through the specimen receiving chamber 134.

Figure 3:
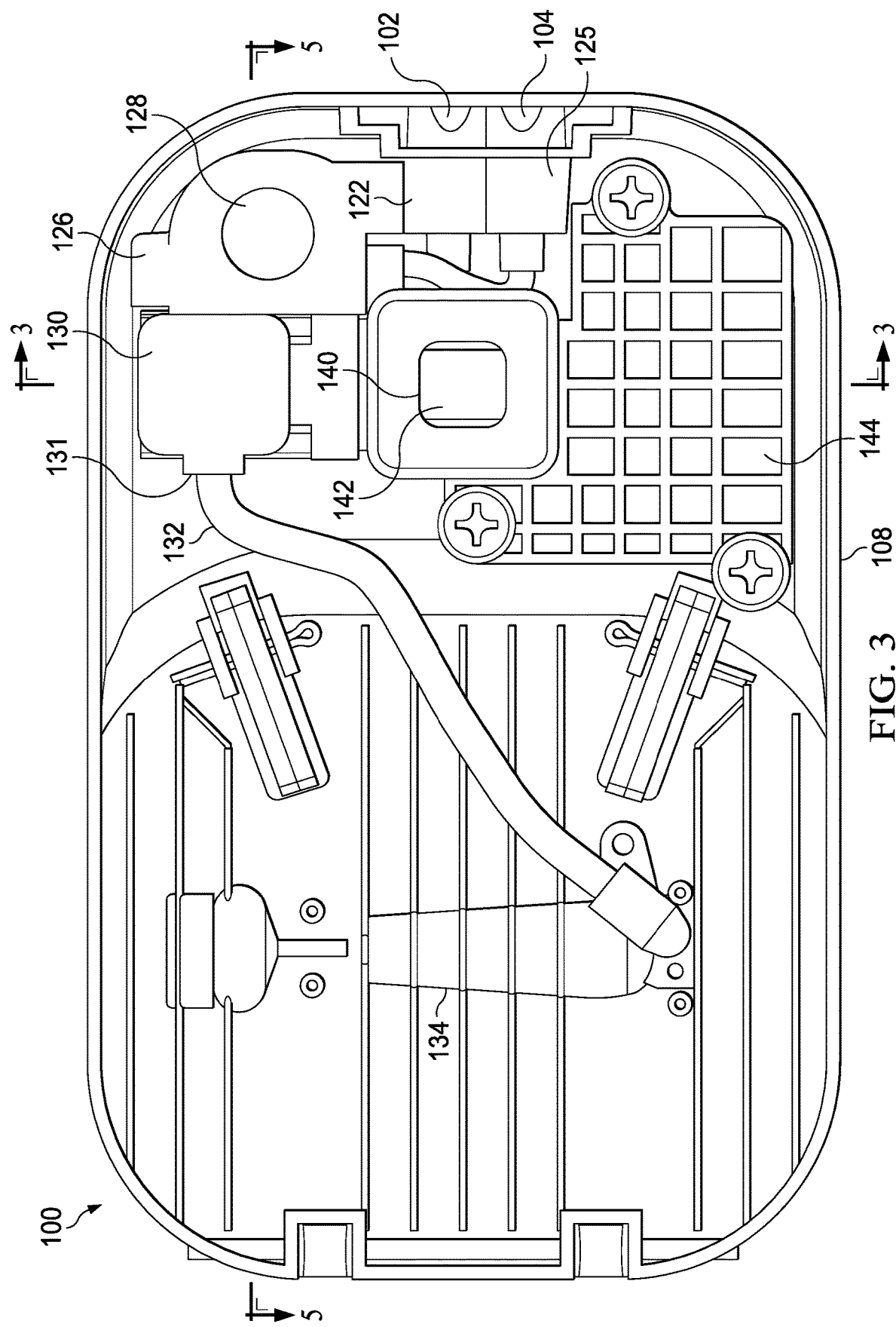
FIG. 3 is a bottom, section view of the specimen delivery cartridge of FIG. 1, as indicated by the lines 3-3 shown in FIG. 5.

FIG. 3 is a section view of the specimen delivery cartridge 100 of FIG. 1 and illustrates operational features of the specimen delivery cartridge 100. This illustration also shows a first actuation port 102 and second actuation port 104 which, respectively, are coupled to or include, and therefore correspond with, a first storage reservoir 122 and a second storage reservoir 124. Here, it is noted that while only two actuation ports and two associated fluid sources are referenced, any suitable number of actuation ports and fluid sources (e.g., n actuation ports and n storage reservoirs may instead be included). Each of the first storage reservoir 122 and second storage reservoir 124 is respectively coupled to a first conduit 146 and second conduit 148 which operates as a fluid coupling (or a respective first fluid inlet and second fluid inlet) to a intermediate reservoir, which may also be referred to as an intermediate reservoir. Each of the first storage reservoir 122 and second storage reservoir 124 may be actuated by an actuation post or similar mechanism that applies a compressive force to the applicable fluid source, thereby motivating a volume of liquid stored within the fluid source(s) to flow through the applicable conduit and into the intermediate reservoir 126.

Figure 4:
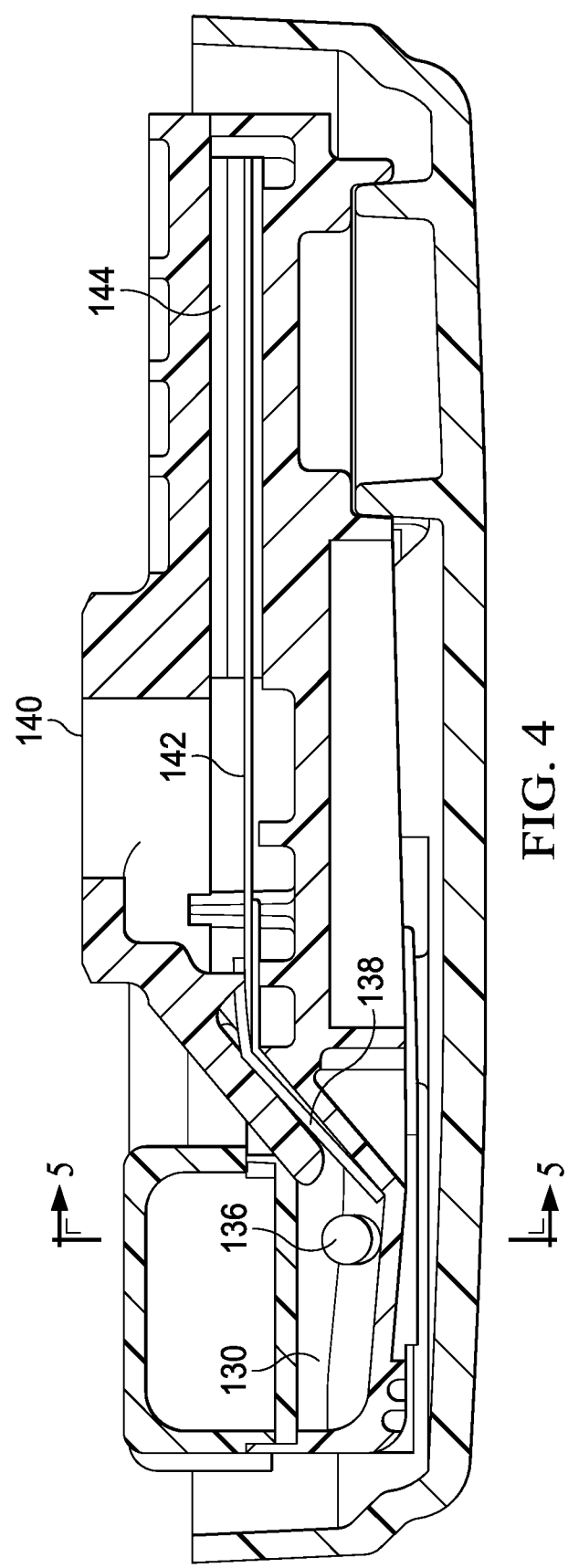
FIG. 4 is a side, section view of the specimen delivery cartridge of FIG. 1, taken along the arrows 4-4 shown in FIG. 5.
Figure 5:
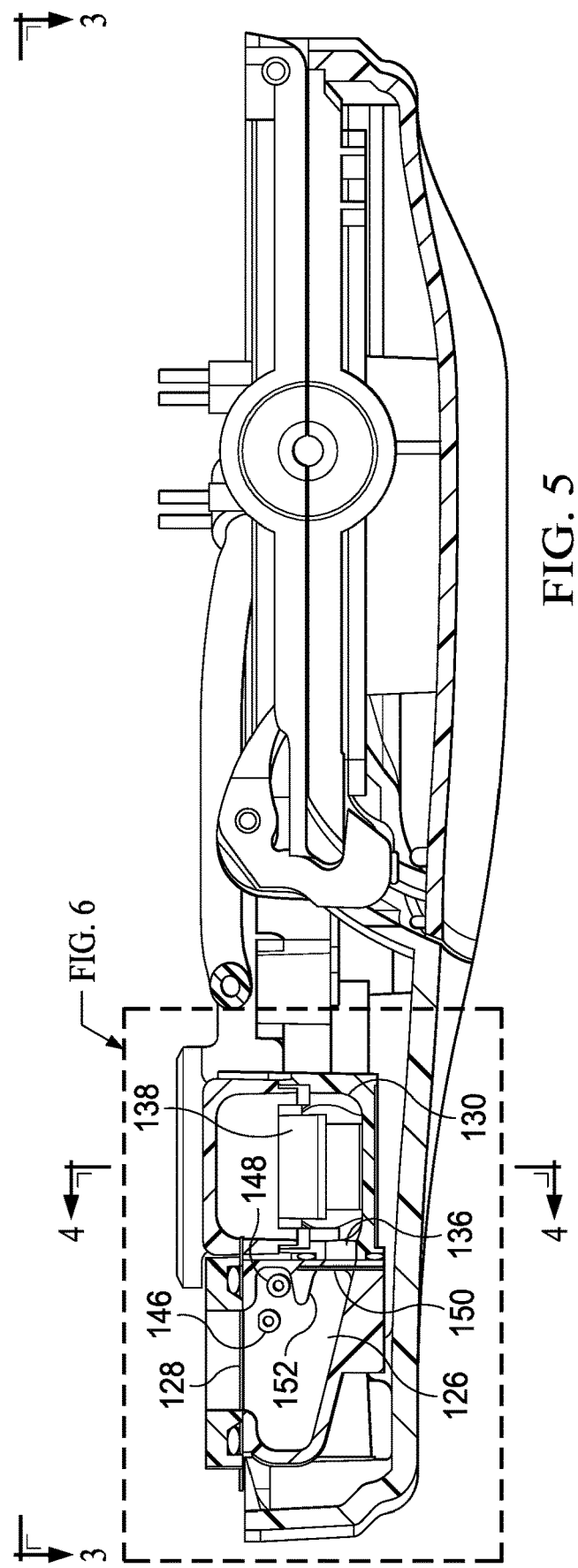
FIG. 5 is a side, section view of the specimen delivery cartridge of FIG. 1, taken along the arrows 5-5 shown in FIGS. 3 and 4.
Figure 6:
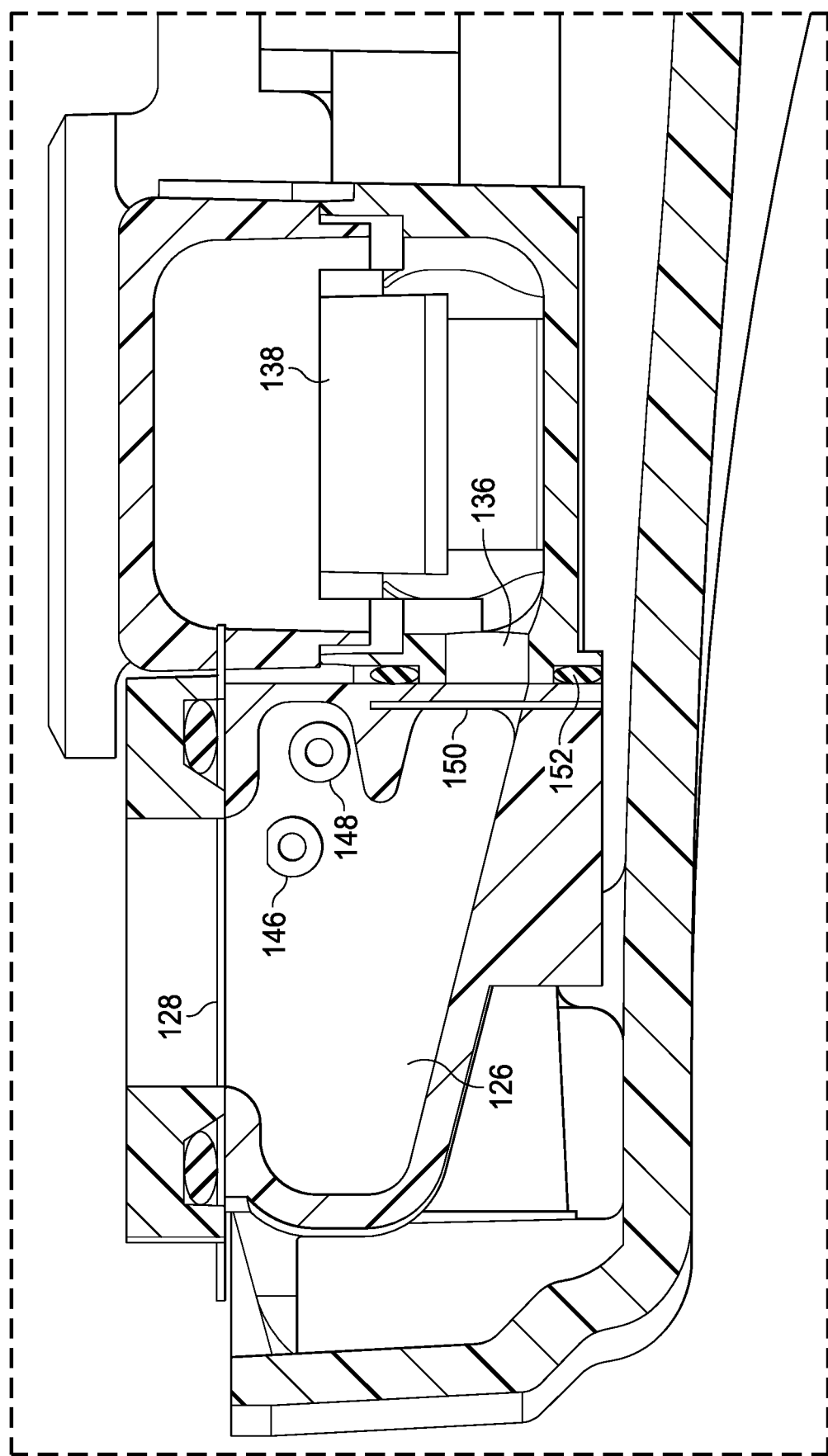
FIG. 6 is a detail, section view of a portion of the specimen delivery cartridge, as indicated in FIG. 5.
Figure 7:
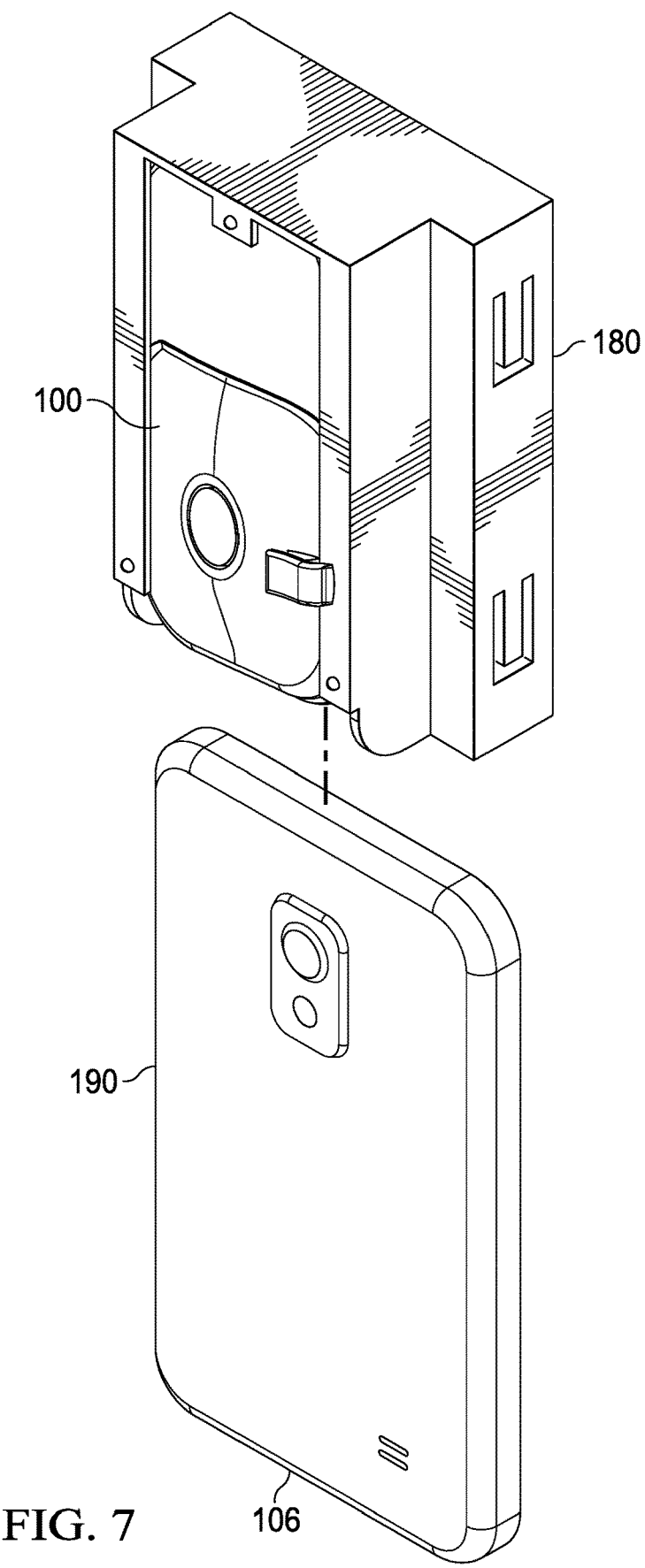
FIG. 7 is an exploded, perspective view showing an assembly of a specimen delivery cartridge with a mating adaptor and a computing device.

The intermediate reservoir 126 is a cavity enclosed at a top surface (when oriented as depicted in FIGS. 4 and 5) by an expandable, elastic diaphragm 128 positioned within a boundary or wall of the intermediate reservoir 126, and at a fluid outlet (intermediate reservoir outlet 136) by a dissolvable membrane 150 or similar frangible device. The dissolvable membrane 150 may be made from a polyvinyl alcohol, or other suitable membrane material. The expandable, elastic diaphragm 128 is operable to expand when one or more pressurized fluids are delivered to the intermediate reservoir 126. In some instances, it may be desirable to allow for mixing of fluids before the fluids are permitted to drain from the intermediate reservoir 126 through the intermediate reservoir outlet 136 and into the downstream reservoir, which may also be referred to as a downstream reservoir 130. Further, in some embodiments it may be desirable to include a baffle 152 between the fluid inlets (first conduit 146 and second conduit 148) of the intermediate reservoir 126 and the dissolvable membrane 150 to minimize the occurrence of premature exposure of the dissolvable membrane 150 to liquids transported into the intermediate reservoir 126 from the fluid inlets.

The downstream reservoir 130 is also fluidly coupled to the specimen receiving chamber 134 by a specimen delivery conduit 132 that is coupled to a specimen inlet 131. The specimen delivery conduit 132 is operable to deliver sample collection liquid that includes the specimen after extraction from a swab or similar specimen collection device to the downstream reservoir 130. The downstream reservoir 130 has a portion of a wicking pad 138 disposed therein that is operable to act as a wicking path from the downstream reservoir 130 across a viewing area 140 toward a fluid sink 144. The viewing area 140 may be a window, lens, or similar viewing feature that allows for visual inspection of the viewing portion 142 of the wicking pad 138. The fluid sink 144 may be a cellulose pad, sponge or other absorbent feature that is operable to provide motivation for fluid to wick from the downstream reservoir 130 to the fluid sink 144. In other embodiments, the fluid sink 144 may be replaced by a fluid outlet to a reservoir that collects a processed liquid for subsequent processing.

In the embodiments shown in the referenced figures, the wicking pad 138 is operable to transport a first liquid, which may be the sample collection liquid received from the specimen receiving chamber 134 across the viewing area 140 at a first time, and a second liquid, which may be a volume of liquid received from the intermediate reservoir 126 across the viewing portion 140 at a second time. The wicking pad 138 may be a cellulose membrane, a glass fiber substrate, or a similar substrate material that facilitates wicking of fluid from the downstream reservoir 130 to the fluid sink 144. More particularly, the wicking pad 138 may be formed from a microfluidic substrate selected from the group consisting of a glass fiber, cellulose paper, nitrocellulose membrane, or a combination thereof.

In some embodiments, a capillary plate apparatus 209, which may alternatively be referred to as a "lateral flow assaying apparatus" may supplant a portion of the wicking pad 138 that passes through the viewing area 140. An example of such a capillary plate apparatus 209 is described with regard to FIGS. 8-10. In embodiments in which the capillary plate apparatus 209 forms a part of the fluid flow path that passes through the viewing area 140, the capillary plate apparatus 209 extends from a first end 220 to a second end 222 of a fluid flow path. The second end 222 of the flow path includes or is coupled to the fluid sink 144, either directly or via an intermediate absorbent pad or wicking material. Similar to embodiments in which a wicking pad 138 extends across the viewing area 140, the fluid sink in such embodiments may be a sponge or similar material that operates as a sink and facilitates the conduction of liquids from the first end 220 to the second end 222 (across the viewing area 140). Between the first end 220 and second end 222, the capillary plate apparatus 209 passes across the referenced viewing area 140, which may also be referred to as a "detection zone." The detection zone may be aligned with an inspection window or similar feature of the specimen processing cartridge 100 (e.g., viewing portion 142) to allow viewing and analysis of the sample during operation.

Figure 8:
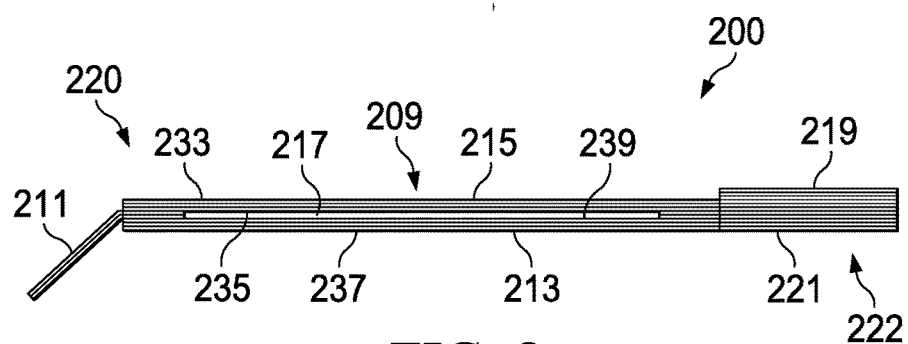
FIG. 8 is a schematic, side-section view of a capillary plate apparatus, or "lateral flow assaying apparatus"
Figure 9:
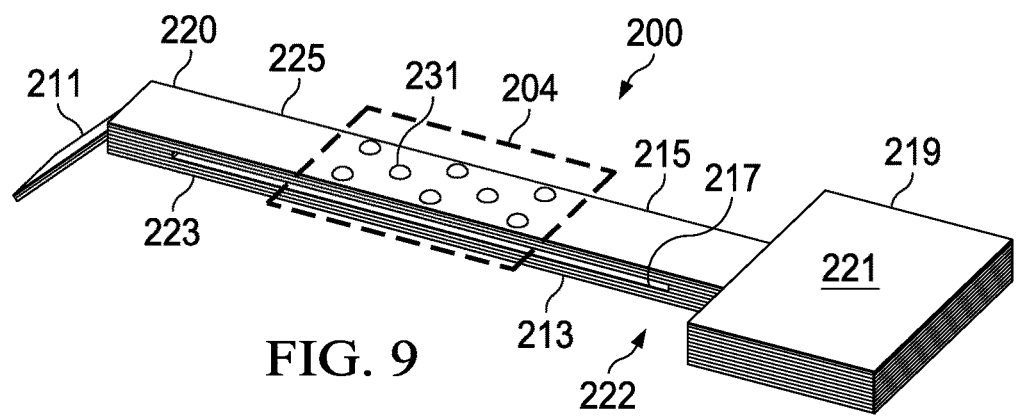
FIG. 9 is a schematic, perspective view of the capillary plate apparatus of FIG. 8.

In the embodiment shown in FIG. 8, the capillary plate apparatus 209 includes or is coupled to an inlet substrate 211 (analogous to the wicking pad 138 described previously) that is sandwiched between a first plate 215 and a second plate 213 (or other inlet to a capillary flow channel). The first plate 215 and second plate 213 may be formed from a hydrophilic polymer, a glass, sapphire, or any other suitable material or a combination thereof. In some embodiments, one or both of the first plate 215 and the second plate 213 may have one or more coatings that enhance capillary action and/or viewability. The first plate 215 includes a viewing surface 233 and an opposing inner surface 235. The second plate 213 includes an outer surface 237 and a second inner surface 239, which may also be referred to as a channel-facing surface. A void 217, which operates as a capillary flow path or "capillary channel," is bounded by (optional) lateral seals at each side of the capillary plate apparatus (see first edge 223 and second edge 225 of FIG. 9), the channel-facing inner surface 235 of the first plate 215, and the channel-facing second inner surface 239 of the second plate 213. At a second end 222, an outlet substrate 219 acts as an interface between the capillary flow path and an absorbent pad 221 that acts as a fluid sink, as described above). A complementary, perspective view is shown in FIG. 9, which further illustrates that a first edge 223 and a second edge 225 of the capillary plate apparatus 209 may be sealed to enclose the capillary flow path. FIG. 9 further illustrates that the capillary plate apparatus 209 may include a detection zone 204, which may correspond to the detection zone or viewing portion 142 described previously.

In alternative embodiments, the capillary flow channel may be formed without the use of plates and may be formed using an alternative structure. In such embodiments, the channel may be formed from, for example, a relatively flattened ellipsoid structure or similar structure. In such embodiments, the "first plate" should be understood to be the portion of the structure that bounds the channel on the side of the structure that faces the viewing area or viewer. Correspondingly, the "second plate" should be understood to be the portion of the structure that bounds the opposing side of the channel.

Figure 10:
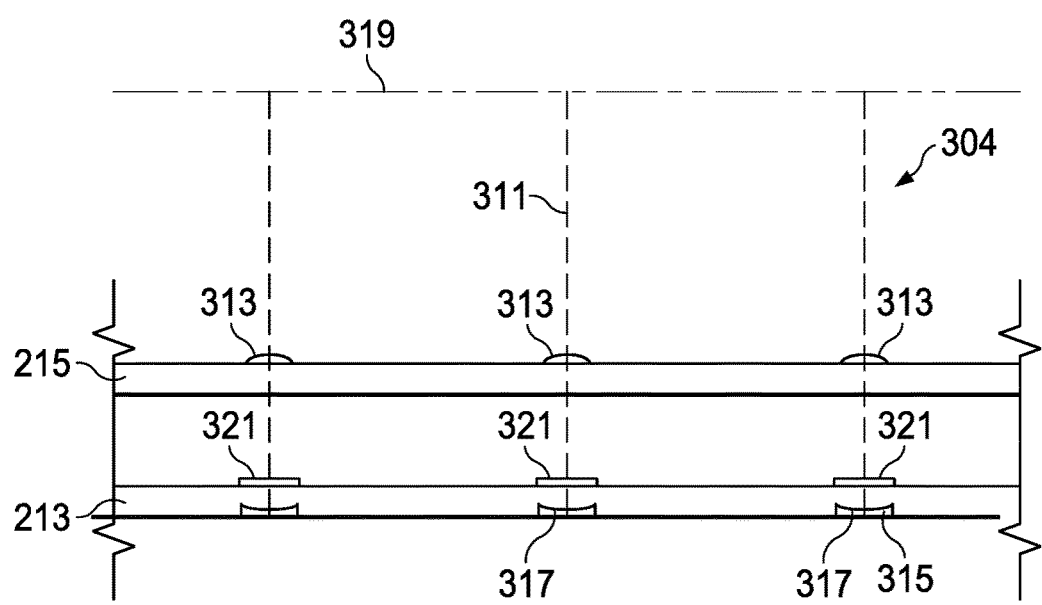
FIG. 10 is a detail, side section view of a viewing area of the capillary plate apparatus of FIG. 8.

A detail view of a representative detection zone 304 is described with regard to FIG. 10. Within the detection zone 304, a lens array may be formed on or in the viewing surface 233, which is proximate to a viewer of the detection zone 304 relative to the outer surface 237. The array of lenses or, lens array 311, includes one or more lenses 313. Correspondingly, a detection locus array 315 may be formed or identified on the second inner surface 239. The detection locus array 315 may include one or more detection locus 317 backing surfaces. The lens array 311 and detection locus array 315 may be arranged such that the center of each lens 313 aligns with the center of a corresponding detection locus 317. Such alignment may be relative to a vector that is perpendicular to the viewing surface 233 or so that the focal points of the lenses are distributed along a common focal plane 319 (such that a plurality of axes extending from each the center of each detection locus 317 and its corresponding lens 313 intersect at the focal plane 319). In this manner, the lenses may be operable to collect chemiluminescent light emanating from the detection loci and to detect or image the collected light along the focal plane, which may involve transmitting the collected through one or more lenses of a mating adapter and onto a CMOS or comparable sensor of a computing device positioned within the mating adapter.

In some embodiments, each of the first plate 215 and the second plate 213 may be formed from a hydrophilic material, such as a clear, hydrophilic polymer. In other embodiments, the channel facing surfaces of the first plate 215 and/or second plate 213 may be coated with a hydrophilic coating. The outer surface 237 or second inner surface 239 of the second plate 213 may also or alternatively be provided with or formed with a metalized coating or other reflective surface coating (or integral reflective property) in order to reflect light back toward the viewer. In some embodiments, the second plate 213 may be made from a reflective material. The coating may be applied broadly across the first surface or at the location one or more of the detection loci 317. Further, each detection locus 317 may correspond to an indentation, which may be a parabolic indentation, a frustoconical, a curved indentation, or any other suitable type of indentation which, in any case, may function to increase the amount of light that is able to be collected a viewed by a detector (e.g., a computing device). Correspondingly, each lens 313 may include curvature that also operates to facilitate light collection and viewing (and corresponding analysis of photoluminescence of a hypothetical assay). In addition to the metalized coating described above, each detection locus 317 or the array of detection loci or (array of indentations) may also be prepopulated with a biological receptor. As referenced herein, a biological receptor is designed to bind with a certain analyte or biologic or chemical target, which after further bio-chemical processing may result in the generation of a detectable biochemical response. Examples of biological receptors include proteins, antibodies and oligonucleotides that facilitate the detection of a target pathogen or other target substance (such as a protein). An example of a biochemical response could be chemiluminescence generated by an ELISA assay format.

It is further noted that while only two plates are shown in FIG. 10, in some embodiments multiple sets of capillary plates may be layered upon each other so that, for example, a first capillary channel having the features described above would overlie a second (or third or fourth or nth) capillary channel also having the features described above. In such an embodiment, the lenses or other focusing features on the various plates may be configured to focus on a common focal plane, so that a single sensor or sensor array may be able to simultaneously analyze signals (e.g., light from one or more chemiluminescent processes). Such an embodiment may provide for the multiplexing of signals or otherwise enhance a device's ability to perform an assaying process using a limited amount of viewing area by allowing detection loci to be placed closer to each other without liquids associated with the loci mixing together in an undesirable manner.

Referring now to the operational aspects of the specimen processing cartridge 100, upon a first actuation event (e.g., a user depressing the actuator 114), the sample collection liquid may be motivated from the first fluid source 121 and through the specimen receiving chamber 134 to strip a biological sample from a collector (e.g., a swab) and to suspend the sample in the first liquid, thereby acquiring the specimen in a suspension or solution. The process of actuating the actuator 114 may provide sufficient pressure to the sample collection liquid to cause the sample collection liquid to flow to the downstream reservoir. These processes may occur when the specimen processing cartridge 100 is oriented approximately as shown in FIG. 1, with the button or bulb that forms the actuator 114 facing upward (relative to gravity) and the specimen processing cartridge 100 being approximately upside-down relative to the orientation depicted in FIG. 4.

The orientation of FIG. 4, and substantially similar orientations may be considered "wicking orientations" that permit liquid to flow out of the downstream reservoir 130 through the wicking pad 138 via an upward wicking action. As a result of the specimen processing cartridge 100 having the described configuration and being in the opposing orientation (in which the sample collection liquid does not contact the wicking pad 138), the sample collection liquid will first be retained in the portion of the downstream reservoir 130 that does not contact the wicking pad 138. When the specimen processing cartridge 100 is flipped over to wicking orientation (substantially as depicted in FIG. 4), the sample collection liquid will contact the wicking pad 138 and begin to flow (via wicking action or a combination of wicking action and capillary flow, as described in more detail below) toward the fluid sink 144. The specimen processing cartridge 100 can thereby be held in the non-wicking position until the user is ready to commence additional processing, at which time the user may flip the specimen processing cartridge 100 to the wicking orientation to begin processing.

Subsequently, contemporaneously, or previously, the user may insert the specimen processing cartridge 100 into a mating adaptor 180 (see FIG. 7) or alternative external device that includes actuation posts that are configured to engage the similar device that include the first storage reservoir 122 and second storage reservoir 124 via the first actuation port 102 and second actuation port 104. The mating adaptor 180 may include separate receiving areas for receiving the specimen processing cartridge 100 and a computing device 190, which may be a cell phone, and include the referenced actuation posts, and is configured such that a camera of the computing device aligns with the viewing area 140 of the specimen processing cartridge 100 when both devices are inserted into the mating adaptor. An example of such a configuration is described in patent application Ser. No. 14/962,998, the subject matter of which is herein incorporated by reference.

Subsequent processes may be actuated by inserting the specimen processing cartridge 100 into the mating adaptor 180 and/or orienting the assembled specimen processing cartridge 100, mating adaptor, and computing device so that the computing device is facing upward toward a user and the specimen delivery cartridge is in the wicking orientation. In the wicking orientation, the sample collection liquid in the downstream reservoir 130 comes into contact with the first end of the wicking pad 138, which wicks the sample collection liquid upward toward viewing area 140 and fluid sink 144. Further, the liquids stored in the first storage reservoir 122 and second storage reservoir 124 are forced by the actuation posts of the mating adaptor into the intermediate reservoir 126. These liquids, having been separated while being stored, are now permitted to mix when in the intermediate reservoir 126.

A intermediate reservoir outlet 136 is positioned similarly to the wicking pad 138, in that the (now) mixed liquid that has been forced into the intermediate reservoir 126 does not contact the dissolvable membrane 150 positioned at the intermediate reservoir outlet 136 until the specimen processing cartridge 100 has been placed in the wicking orientation.

In some embodiments, the liquid stored in the first storage reservoir 122 is luminol and the liquid stored in the second storage reservoir 124 is hydrogen peroxide that is operable to mix with the luminol. The mixed liquid may provide illumination at the testing area in the presence of a target pathogen-detecting antibody-capture antibody complex owing to the functionalization of the detection antibody with an enzyme, such as horseradish peroxidase (HRP). This may result in the generation of a chemiluminescent signal upon reaction with the previously described luminol-$H_2O_2$ mixture as the mixture progresses over the detection zone (either due to wicking or capillary action).

As noted above, the dissolvable membrane 150 serves, in combination with (optional gasketing) at the intermediate reservoir outlet 136, to form a frangible, sealed interface between the intermediate reservoir 126 and downstream reservoir 130. The dissolvable membrane 150 thereby occludes flow through the intermediate reservoir fluid outlet 136 when the dissolvable membrane 150 is in a first, undissolved state, and permits flow from the intermediate reservoir 126 to the downstream reservoir 130 when in a second, dissolved state.

The dissolvable membrane 150 may operate as a timing mechanism because the membrane material is selected to have a composition and thickness that is operable to dissolve after a desired, predetermined amount of time after the membrane has been exposed to the liquid in the downstream reservoir 130 (i.e., the mixed liquid referenced above). Moreover, the application of hydraulic force from the actuation posts may result in the application of increased pressure at the intermediate reservoir 126, which may in turn result in the expansion of the expandable, elastic diaphragm 128. The expansion of the expandable, elastic diaphragm operates as a store of potential energy until the dissolvable membrane ruptures, at which point elastomeric properties of the expandable, elastic diaphragm 128 cause the expandable, elastic diaphragm 128 to apply a hydraulic force that motivates the mixed liquid from the intermediate reservoir 126 to the downstream reservoir 130.

Prior to dissolution of the dissolvable membrane 150, however, the wicking properties of the wicking pad 138 facilitate conduction of the sample collection liquid (that now includes the suspended or dissolved specimen) across the viewing area 140 and excess liquid is absorbed at the fluid sink 144. In some embodiments, dried reagents may be pre-deposited on (or affixed to) the portion of the wicking pad 138 that underlies the viewing area 140 (i.e., at the detection zone). Those reagents may attract and/or interact with particles of the sample as the sample collection liquid flows across the wicking pad 138.

After a desired time delay, dissolution of the dissolvable membrane 150 and hydraulic force provided by the expandable, elastic diaphragm 128 result in the mixed liquid from the intermediate reservoir 126 flowing through the intermediate reservoir outlet 136 and into the downstream reservoir 130. The mixed liquid may be a wash, and active solution (e.g., a luminol peroxide), a lysing agent, or a reagent suspension that is operable to interact with particles from the specimen at the viewing area 140. The mixed liquid may be formed by mixing (for example) a liquid from the first storage reservoir 122 with a liquid from the second storage reservoir 124. In addition, or in the alternative, additional fluid sources and corresponding actuation posts, secondary reservoirs, and dissolvable membranes may be provided so that any number of different liquids may be delivered in series or in parallel (as determined by the time delay corresponding to the applicable dissolvable membrane(s)) to the downstream reservoir 130 and, correspondingly, the wicking pad 138. For the purposes of brevity, however, only a single mixed liquid and a single intermediate reservoir are discussed.

In some embodiments, the mixed liquid is selected to be a wash, an active solution that is operable to displace the sample collection liquid, or an active solution operable interact with sample particles or reagent at the viewing area 140. If used, additional fluid may also include for example, a lysing agent or a reagent that may interact with target pathogens to cause a reaction that reveals the presence of the target.

In some embodiments, the mixed liquid, or a second or other liquid that is subsequently delivered to the viewing area 140, may be a liquid that facilitates viewing of the test carried out at the viewing area 140, such as a luminol peroxide. In such embodiments, the luminol peroxide may be used to interact with a portion of a specimen after initial processing to initiate a chemiluminescent reaction that may be observed to determine whether a target pathogen is present. In some embodiments, one or more pre-dried reagents are placed at predetermined locations on the portion of the wicking pad 138 that underlies the viewing area. The pre-dried reagents may be operable to react with one or more of the sample, the mixed fluid, or another fluid that wicks across the wicking pad 138.

Operation of the specimen processing cartridge 100 may further include analyzing the viewing area 140 after the sample collection liquid (including the specimen) has wicked across the viewing area 140 or at a later time when both of the sample collection liquid and the mixed liquid have wicked across the viewing area. The analysis may include analyzing one or more locations of the wicking pad 138 where the sample collection liquid, mixed liquid, and (optionally) one or more subsequent liquids may have interacted with one another or with one or more pre-dried reagents positioned on the wicking pad 138 to determine whether a target substance or pathogen was present in the specimen. The foregoing method may be iterative and to that end, may involve any number of secondary liquids using the time-delay mechanisms described above to achieve an ordered and timed sequence of liquid interactions. For example, in some embodiments, a second fluid may be a wash fluid and a third fluid may include a reagent that interacts with portions of the wicking pad that are populated with a binding agent that captures portions of the specimen from the sample collection liquid.

In some embodiments, each of the one or more fluid sources (e.g., first storage reservoir 122, second storage reservoir 124, . . . and nth storage reservoir) be actuated simultaneously to deliver liquids to the wicking pad 138 in a timed sequence based on differences in time for which a respective dissolvable membrane ruptures in the presence of the applicable liquid. The such embodiments, the fluid sources may deliver fluid to downstream reservoirs that are included by, for example, dissolvable membranes of different thicknesses. In such embodiments, the sample collection liquid may be delivered to the wicking pad 138 at a first time, a second or mixed fluid may be delivered to the wicking pad 138 at a second time that is later than the first time, a third fluid may be delivered to the wicking pad 138 at a third time that is later than the second time, and so on.

In embodiments in which the wicking pad is coupled to a capillary plate apparatus, the wicking properties of the wicking pad 138 may conduct the liquids to the capillary plate apparatus (209), thereby dispersing the first liquid along with particles of the sample to detection locations that are deposited across portions of the backing surface of the detection loci 317. In some embodiments, dried reagents may be pre-deposited on (or affixed to) the second plate 213 at the detection zone 204 attract and/or interact with particles of the sample included in the sample collection liquid flow across the capillary plate apparatus.

In any event, the mixed or another secondary liquid may be conducted across the viewing area 140, and may be a wash, or an active solution that is operable to displace the first liquid and optionally to interact with sample particles or reagent at the viewing area 140. The second liquid may include, for example, a lysing agent or a reagent that may interact with target pathogens to cause a reaction that reveals the presence of the target. The reaction sequence may be selected to such that the sample particles interact with reagents or receptors at the viewing area 140 to provide a visual indication of the presence or absence of a target pathogen in the sample, which may be detected visually by a user or using the lens and camera functionality of a computing device (e.g., a mobile device or smartphone).

It is noted that unless an embodiment is expressly stated as being incompatible with other embodiments, the concepts and features described with respect to each embodiment may be applicable to and applied in connection with concepts and features described in the other embodiments without departing from the scope of this disclosure. To that end, the above-disclosed embodiments have been presented for purposes of illustration and to enable one of ordinary skill in the art to practice the disclosure, but the disclosure is not intended to be exhaustive or limited to the forms disclosed. Many insubstantial modifications and variations will be apparent to those of ordinary skill in the art without departing from the scope and spirit of the disclosure. The scope of the claims is intended to broadly cover the disclosed embodiments and any such modification.

As used herein, the singular forms "a", "an" and "the" are intended to include the plural forms as well, unless the context clearly indicates otherwise. It will be further understood that the terms "comprise" and/or "comprising," when used in this specification and/or the claims, specify the presence of stated features, steps, operations, elements, and/or components, but do not preclude the presence or addition of one or more other features, steps, operations, elements, components, and/or groups thereof. In addition, the steps and components described in the above embodiments and figures are merely illustrative and do not imply that any particular step or component is a requirement of a claimed embodiment.

The invention claimed is:

1. A specimen processing cartridge comprising:
    an intermediate reservoir having a fluid inlet, an elastic diaphragm, and a fluid outlet, the intermediate reservoir being operable to receive a volume of liquid from the fluid inlet, and the fluid outlet being positioned along a fluid flow path between the fluid inlet and a downstream reservoir; and
    a dissolvable membrane that occludes the fluid outlet when the dissolvable membrane is in a first, undissolved state, and that permits flow from the intermediate reservoir to the downstream reservoir when in a second, dissolved state,
    wherein the fluid inlet is positioned below the fluid outlet and dissolvable membrane when the specimen processing cartridge is in a first orientation, the first orientation opposing a wicking orientation,
    wherein the fluid inlet is positioned above the fluid outlet when the specimen processing cartridge is placed in the wicking orientation, and
    wherein the elastic diaphragm is operable to pressurize the intermediate reservoir upon receiving the volume of liquid when the dissolvable membrane is in the first, undissolved state, and wherein the elastic diaphragm is operable to contract and propel at least a portion of the volume of liquid from the intermediate reservoir to the downstream reservoir when the dissolvable membrane is in the second, dissolved state.

2. The specimen processing cartridge of claim 1, wherein the intermediate reservoir comprises a baffle positioned between the fluid inlet and the fluid outlet.

3. The specimen processing cartridge of claim 1, further comprising:
    at least one storage reservoir, each of the at least one storage reservoir being positioned within a corresponding actuation port that is operable to receive a corresponding actuation post positioned on an external device,
    wherein the specimen processing cartridge is operable to apply a hydraulic force to each of the at least one storage reservoir upon insertion of the corresponding actuation post into the corresponding actuation port, and
    wherein application of the hydraulic force to each of the at least one storage reservoir propels a liquid stored within each of the at least one storage reservoir into the intermediate reservoir and positively pressurizes the intermediate reservoir.

4. The specimen processing cartridge of claim 3, wherein:
    the at least one storage reservoir comprises a first storage reservoir having a first liquid disposed therein and a second storage reservoir having a second liquid disposed therein,
    wherein application of the hydraulic force to each of the first storage reservoir and the second storage reservoir propels the first liquid and the second liquid into the intermediate reservoir to form the volume of liquid.

5. The specimen processing cartridge of claim 1 further comprising:
    a collection liquid reservoir operable to store a sample collection liquid and being coupled to an actuator;
    a specimen receiving chamber operable to receive a sample collection device, the specimen receiving chamber being fluidly coupled to the collection liquid reservoir and operable to receive the sample collection liquid upon actuation of the actuator;
    a fluid coupling extending from the specimen receiving chamber to the downstream reservoir;
    a fluid flow path extending from the downstream reservoir, across a viewing area, and to a fluid sink.

6. The specimen processing cartridge of claim 5, wherein the fluid flow path comprises a wicking pad that is operable to receive liquid from the downstream reservoir, and wherein a first portion of the wicking pad is positioned below the viewing area when the specimen processing cartridge is in the wicking orientation.

7. The specimen processing cartridge of claim 5, wherein a portion of the fluid flow path that extends across the viewing area comprises a capillary plate assaying apparatus fluidly coupled to a wicking pad and operable to facilitate capillary flow from the wicking pad to the fluid sink.

8. A method for implementing a diagnostic process comprising:

delivering a volume of liquid to an intermediate reservoir of a diagnostic device via a fluid inlet, the diagnostic device comprising: the intermediate reservoir, an elastic diaphragm positioned within a boundary of the intermediate reservoir, a fluid outlet port positioned along a fluid flow path between the fluid inlet and a downstream reservoir, and a dissolvable membrane that occludes the fluid flow path when the dissolvable membrane is in a first, undissolved state, and that permits flow from the intermediate reservoir to the downstream reservoir when in a second, dissolved state;

applying a positive pressure to the intermediate reservoir, thereby causing expansion of the elastic diaphragm when the dissolvable membrane is in the first, undissolved state; and exposing the dissolvable membrane to the volume of liquid, wherein the dissolvable membrane dissolves after a predetermined amount of time lapses following exposure to the volume of liquid, wherein the fluid inlet is positioned below the fluid outlet and dissolvable membrane when the diagnostic device is in a first orientation, the first orientation opposing a wicking orientation, wherein the fluid inlet is positioned above the fluid outlet when the diagnostic device is placed in the wicking orientation, and wherein dissolution of the dissolvable membrane permits the elastic diaphragm to contract and propel at least a portion of the volume of liquid from the intermediate reservoir to the downstream reservoir.

9. The method of claim 8, wherein the volume of liquid comprises a reagent.

10. The method of claim 8, wherein the dissolvable membrane comprises polyvinyl alcohol.

11. The method of claim 8, wherein the diagnostic device further comprises at least one storage reservoir positioned within a corresponding at least one actuation port, the method further comprising:

inserting the diagnostic device into a mating adaptor having at least one actuation post corresponding to each of the at least one actuation port, wherein the step of inserting the diagnostic device into the mating adaptor comprises applying a hydraulic force to each of the at least one storage reservoir by receiving at least one actuation post into the corresponding at least one actuation port, wherein application of the hydraulic force propels a stored liquid within each of the at least one storage reservoir into the intermediate reservoir and positively pressurizes the intermediate reservoir.

12. The method of claim 11, wherein:

the at least one storage reservoir comprises a first storage reservoir having a first liquid disposed therein and a second storage reservoir having a second liquid disposed therein, wherein the application of the hydraulic force to each of the first storage reservoir and the second storage reservoir propels the first liquid and the second liquid into the intermediate reservoir to form the volume of liquid.

13. The method of claim 8, wherein the diagnostic device further comprises a collection liquid reservoir operable to store a sample collection liquid and being coupled to an actuator, a specimen receiving chamber operable to receive a sample collection device and being fluidly coupled to the collection liquid reservoir and operable to receive the sample collection liquid upon actuation of the actuator, a fluid coupling extending from the specimen receiving chamber to the downstream reservoir, and a fluid flow path extending from the downstream reservoir, across a viewing area, and to a fluid sink, wherein the method further comprises activating the actuator and propelling the sample collection liquid from the collection liquid reservoir, through the specimen receiving chamber, and to the downstream reservoir.

14. The method of claim 13, wherein the fluid flow path comprises a wicking pad that is operable to receive liquid from the downstream reservoir, and wherein a first portion of the wicking pad is positioned below the viewing area when the diagnostic device is in a wicking orientation, and wherein the diagnostic device further comprises at least one storage reservoir positioned within a corresponding at least one actuation port, the method further comprising:

inserting the diagnostic device into a mating adaptor having at least one actuation post corresponding to each of the at least one actuation port; and orienting the mating adaptor above the diagnostic device, wherein the step of inserting the diagnostic device into the mating adaptor comprises applying a hydraulic force to each of the at least one storage reservoir by receiving at least one actuation post into the corresponding at least one actuation port, wherein application of the hydraulic force propels a liquid stored within each of the at least one storage reservoir into the intermediate reservoir and positively pressurizes the intermediate reservoir.

15. The method of claim 14, wherein a portion of the fluid flow path that extends across the viewing area comprises a capillary plate assaying apparatus fluidly coupled to the wicking pad and operable to facilitate capillary flow from the wicking pad to the fluid sink.

16. The method of claim 14, wherein the step of orienting the mating adaptor above the diagnostic device results in the sample collection liquid flowing across the viewing area at a first time prior to dissolution of the dissolvable membrane and the volume of liquid flowing across the viewing area at a second time following dissolution of the dissolvable membrane.

* * * * *